United States Patent [19]

Shito

[11] Patent Number: 5,183,060
[45] Date of Patent: Feb. 2, 1993

[54] DEVICE FOR PROTECTING PORTION BETWEEN TOES

[76] Inventor: Souichi Shito, 1-38-7, Kamakura, Katsushika-ku, Tokyo, Japan

[21] Appl. No.: 659,651

[22] Filed: Feb. 25, 1991

[30] Foreign Application Priority Data

May 11, 1990 [JP] Japan .................. 2-49429[U]
Jul. 23, 1990 [JP] Japan .................. 2-77944[U]
Oct. 12, 1990 [JP] Japan ................ 2-107084[U]

[51] Int. Cl.⁵ .............................................. A61F 5/00
[52] U.S. Cl. ................................... 128/882; 128/894; 602/56
[58] Field of Search .............. 128/889, 892, 893, 894; 36/71, 94; 602/41, 56

[56] References Cited

U.S. PATENT DOCUMENTS

| | | | |
|---|---|---|---|
| 1,245,253 | 11/1917 | Marglous | 128/893 X |
| 1,476,682 | 12/1923 | Beckman | 128/894 |
| 1,806,998 | 5/1931 | Kaufman | 128/894 |
| 1,874,737 | 8/1932 | Boisselier | 128/894 |
| 2,115,237 | 4/1938 | Scholl | 128/893 |
| 2,161,720 | 6/1939 | Morelli | 128/894 |
| 2,595,640 | 5/1952 | Christopoulos | 128/893 X |
| 2,640,482 | 6/1953 | Kiwad | 128/893 |
| 2,655,917 | 10/1953 | Kiwad | 128/893 |
| 4,877,018 | 10/1989 | Ikebe et al. | 128/893 X |

FOREIGN PATENT DOCUMENTS

| | | | |
|---|---|---|---|
| 531377 | 11/1957 | Belgium | 128/893 |
| 0268190 | 10/1913 | Fed. Rep. of Germany | 128/893 |
| 592241 | 7/1925 | France | 128/894 |

Primary Examiner—Robert A. Hafer
Assistant Examiner—Sam Rimell
Attorney, Agent, or Firm—Armstrong, Westerman, Hattori, McLeland & Naughton

[57] ABSTRACT

A toe-base protecting device which comprises a toe-base protecting member comprising a hygroscopic and flexible non-woven fabric, paper, cloth or fibers formed into a substantially rod-like shape, and two adhesive members that are attached to both ends, respectively, of the protecting member, the adhesive members being stuck on the top and bottom surfaces, respectively, of a foot with the protecting member being put between toes.

7 Claims, 9 Drawing Sheets

DEVICE FOR PROTECTING PORTION BETWEEN TOES

BACKGROUND OF THE INVENTION

The present invention relates to a toe-base protecting device which is designed to dry the base portion between a pair of adjacent ones of the five toes so as to relieve it from sweatiness and dampness.

The base portion between a pair of adjacent toes readily gets sweaty because the two adjacent toes are likely to come into close contact with each other.

For this reason, the base portion between a pair of adjacent toes is likely to develop ringworm, for example, athlete's foot.

It is therefore necessary to dry the base portion between toes.

Figure 12:
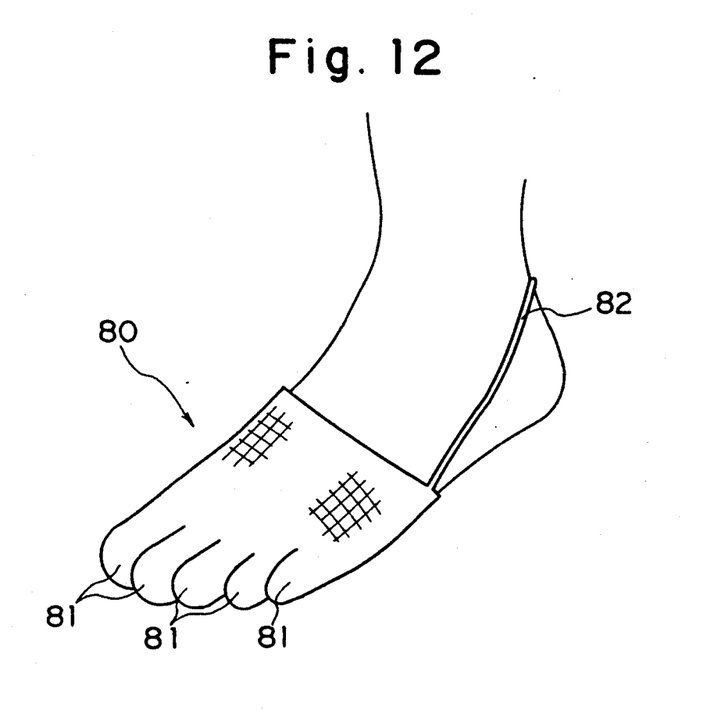
FIG. 12 is a perspective view of a conventional toe-base protecting device.

FIG. 12 is a perspective view of a conventional toe-base protecting device which is designed to dry a portion between toes.

As illustrated, the conventional toe-base protecting device 80 comprises a bag-shaped member which is formed from a piece of gauze or cotton cloth in the shape of a bag so as to wrap the toe-side half of a foot. The bag-shaped member is provided at the closed end with bag-shaped toe insertion portions 81 for wrapping the respective toes of a foot. In addition, a rubber strap 82 is attached to the open end of the bag-shaped member to secure the device 80 in position by catching the strap 82 on the heel.

With the above-described arrangement, the gauze or cotton cloth is interposed between the toes, thereby enabling the portion between each pair of adjacent toes to be dried.

Figure 13:
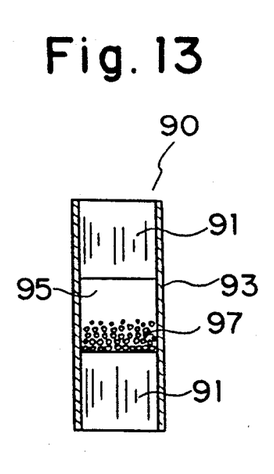
FIG. 13 is a sectional view of another conventional toe-base protecting device.

FIG. 13 is a sectional view of another conventional toe-base protecting device (U.S. Pat. No. 4,877,018).

As illustrated, the toe-base protecting device 90 comprises two fibrous layers 91 each comprising a bundle of a large number of fibers which are longitudinally put close together in a columnar shape, the two fibrous layers 91 being vertically spaced at a suitable distance. A flexible shell member 93 is wound around the peripheries of the upper and lower fibrous layers 91 to define a cavity portion 95 therebetween, and particulate substances 97 having a hygroscopic function are accommodated in the cavity portion 95.

Figure 14:
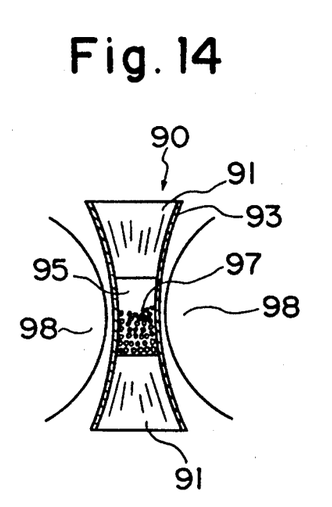
FIG. 14 is a sectional side view of the toe-base protecting device, shown in FIG. 13, which is in actual use.

In use, the device 90 is put on the base portion between two toes 98 and sandwiched therebetween in such a manner that the upper and lower fibrous layers 91 are disposed at the upper and lower sides, respectively, of the area between the two toes 98, as shown in FIG. 14, to dry the base portion between the toes 98 by means of the particulate substances 97.

The device 80 shown in FIG. 12 suffers, however, from the problem that, since the gauze or cotton cloth is thin, the base portion between each pair of adjacent toes cannot be relieved from sweatiness and dried satisfactorily.

In addition, since the device 80 is structured to cover the toe-side half of a foot completely with gauze or cotton cloth, it is bulky, and if the user wears a sock over the device 80, it pinches his or her foot.

On the other hand, the device 90 shown in FIG. 13 involves the problem that, since the fibrous layers 91 project to the upper and lower sides of the toes 98, as shown in FIG. 14, if the user walks with the device 90 put between the toes 98, the lower fibrous layer 91 is pushed up when the foot is set on the ground, causing the toes 98 to be pushed up, which makes the user feel uncomfortable.

In addition, since users are different from each other in the shape of the portion between toes, the level of pressure applied to each toe and the way in which each toe bends and stretches when the user walks, the device 90, which is merely put between two toes, may come off the area between the toes when the user walks or takes exercise for a long time, resulting in the effectiveness being lost.

SUMMARY OF THE INVENTION

It is an object of the present invention to provide a device for protecting a portion between toes which is designed so that the base portion between two toes can be satisfactorily and thoroughly dried, and even if the user wears a sock or/and a shoe over the device, it will not pinch the foot, and moreover, the user can walk or take exercise for a long time without feeling uncomfortable with the device and without any possibility of the device coming off the area between the two toes.

The present invention provides a toe-base protecting device which comprises a toe-base protecting member comprising a hygroscopic and flexible non-woven fabric, paper, cloth or fibers formed into a substantially rod-like shape, and two adhesive members that are attached to both ends, respectively, of the protecting member, the adhesive members being stuck on the top and bottom surfaces, respectively, of a foot with the protecting member being put between toes.

In addition, the present invention provides a toe-base protecting device which comprises a toe-base protecting member comprising a hygroscopic and flexible non-woven fabric, paper, cloth or fibers formed into a substantially rod-like shape, a supporter having one end of the protecting member attached thereto, the supporter being fixedly wound around the substantially central portion of a foot, and a strip of adhesive tape that is attached to the other end of the protecting member.

In addition, the present invention provides a toe-base protecting device which comprises a toe-base protecting member comprising a hygroscopic and flexible non-woven fabric, paper, cloth or fibers formed into a substantially rod-like shape, and a supporter having both ends of the protecting member attached thereto, the supporter being fixedly wound around the substantially central portion of a foot.

With the toe-base protecting device of the present invention, both ends of the toe-base protecting member can be reliably secured to the top and bottom surfaces of a foot by the adhesive members or the supporter with the protecting member being reliably brought into close contact with the base portion between toes. Accordingly, the two toes will not come into close contact with each other at the base portion and an adequate gap can be maintained between the toes. It is therefore possible not only to dry satisfactorily the base portion between the toes but also to protect a part of the base portion which is affected by trichophytosis.

In addition, the toe-base protecting device of the present invention has a simple structure and is easy to attach and detach, so that it can be readily removed and replaced every day.

Since the toe-base protecting device of the present invention is fitted only to the base portion between toes, it will not make the user feel cramped even if he or she wears a sock or/and a shoe over the device.

Since both ends of the toe-base protecting member are reliably secured to the foot by the adhesive members or the supporter, there is no possibility of the device coming off, and the user can walk with less uncomfortableness.

DESCRIPTION OF THE PREFERRED EMBODIMENTS

(First Embodiment)

Figure 1A:
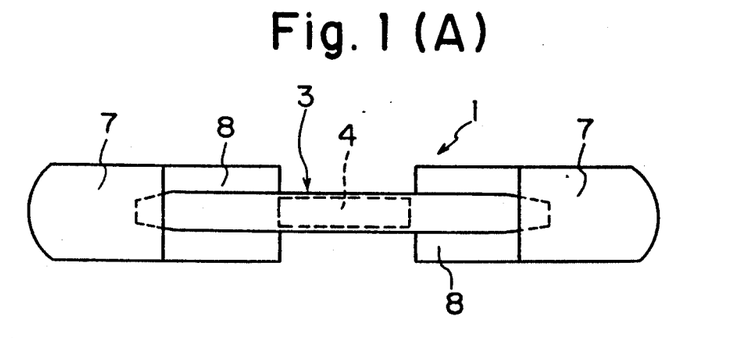
FIGS. 1(A) and 1(B) are plan and side views showing a first embodiment of the toe-base protecting device according to the present invention.
Figure 1B:
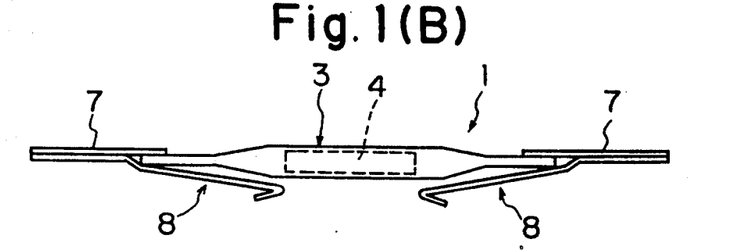

FIG. 1(A) is a plan view of a toe-base protecting device 1 according to a first embodiment of the present invention, and FIG. 1(B) is a side view of the device 1.

As illustrated, the device 1 comprises a toe-base protecting member 3 that is formed in a substantially rod-like shape and two strips 7 of adhesive tape, which are attached to two ends, respectively, of the toe-base protecting member 3.

FIG. 2 shows a procedure for producing the device 1. A method of producing the device 1 will be explained below with reference to FIG. 2.

Figure 2A:
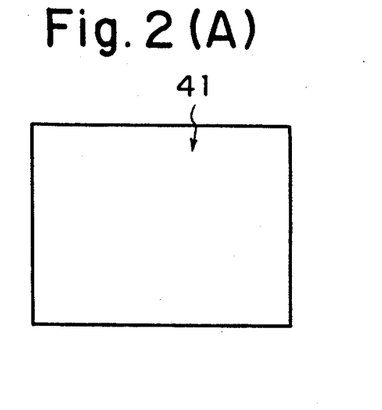
FIGS. 2(A) to 2(F) show a procedure for producing the toe-base protecting device shown in FIG. 1.

Referring first to FIG. 2(A), a non-woven fabric 41 which is thin, flexible and hygroscopic is prepared. The non-woven fabric 41 has a rough surface. Hygroscopic paper or cloth, e.g., gauze, may be employed in place of the non-woven fabric 41.

Figure 2B:
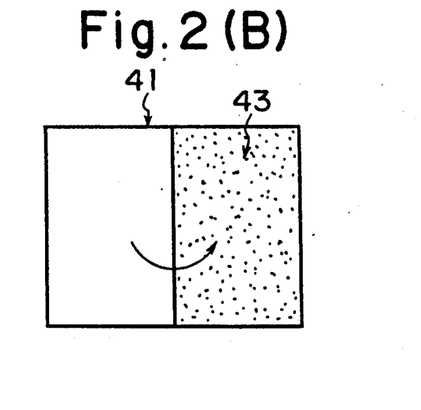

Next, activated carbon particles or powder 43 is uniformly scattered over the surface of the right half of the non-woven fabric 41, as shown in FIG. 2(B).

Figure 2C:
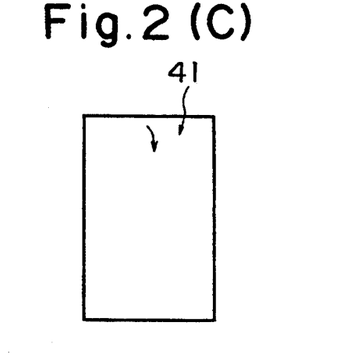

Next, the left half of the non-woven fabric 41 is folded over the right half, as shown in FIG. 2(C).

Figure 2D:
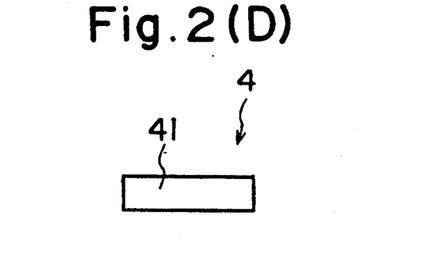

Next, the folded fabric 41 is rolled up into a substantially rod-like shape to form a drying member 4, as shown in FIG. 2(D).

Figure 2E:
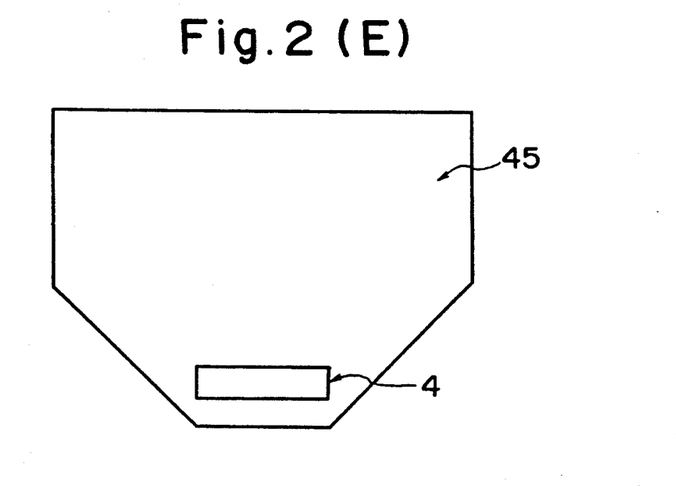

Next, a non-woven fabric 45 which is made of the same material as that of the non-woven fabric 41 is prepared, and the drying member 4 is placed on the lower end of the central portion of the fabric 45, as shown in FIG. 2(E).

Figure 2F:
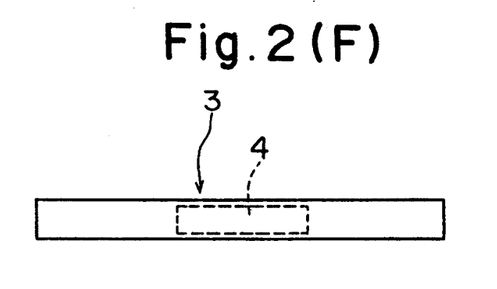

Next, the non-woven fabric 45 is rolled up into a substantially rod-like shape, thus completing a toe-base protecting member 3, as shown in FIG. 2(F).

Then, two strips 7 of adhesive tape are stuck to two ends, respectively, of the toe-base protecting member 3, as shown in FIG. 1, thus completing a toe-base protecting device 1.

It should be noted that release paper 8 is attached to the lower side of each strip 7 of adhesive tape.

Figure 3A:
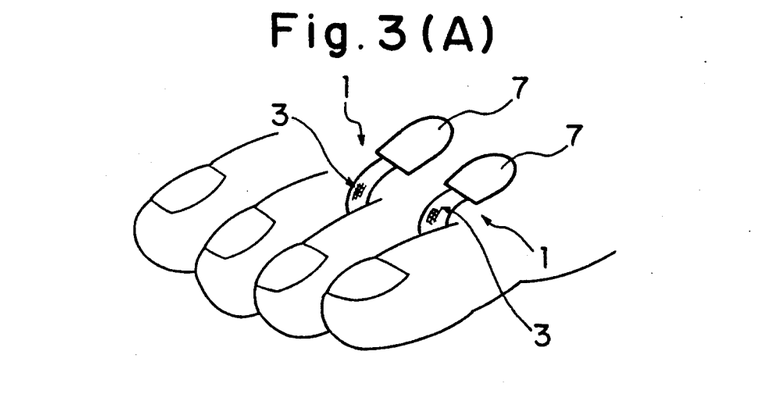
FIGS. 3(A) and 3(B) show a way of using the toe-base protecting device shown in FIG. 1.
Figure 3B:
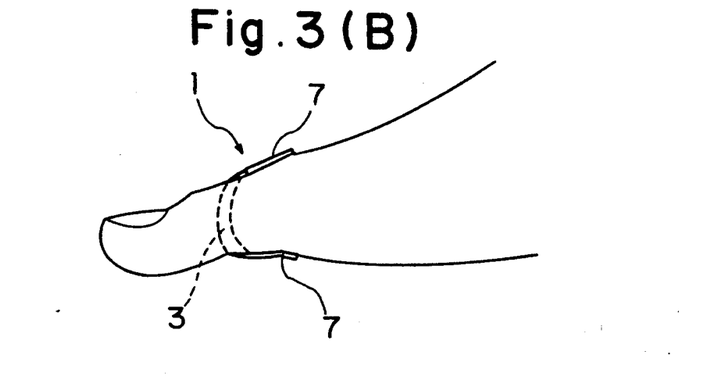

FIGS. 3(A) and 3(B) are perspective and side views showing a way of using the device 1.

To attach the device 1 to a foot, the toe-base protecting member 3 is put on the base portion between two desired toes and sandwiched therebetween, as illustrated. Next, two ends of the protecting member 3 are pulled so that the drying member 4 in the protecting member 3 is pressed against the base portion between the toes, and while doing so, the release paper 8 is separated, and one strip 7 of adhesive tape is stuck on the instep, while the other strip 7 of adhesive tape is stuck on the sole.

By attaching the device 1 to a portion between two toes in this way, this portion is effectively dried by the activated carbon in the drying member 4 and the non-woven fabric that constitutes the toe-base protecting member 3.

Since the activated carbon particles or powder in the drying member 4 is uniformly scattered over the non-woven fabric, which is folded and rolled up, the particles or powder remains uniformly distributed in the drying member 4 without gathering in one place, thus enabling the portion between two toes to be dried efficiently.

Although in the first embodiment activated carbon is scattered over the non-woven fabric, hygroscopic particles or powder may be used in place of it.

(Second Embodiment)

Figure 4A:
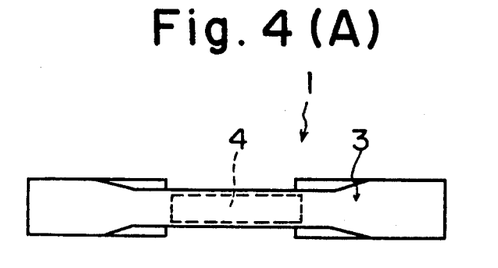
FIGS. 4(A) and 4(B) are plan and side views showing a second embodiment of the toe-base protecting device according to the present invention.
Figure 4B:
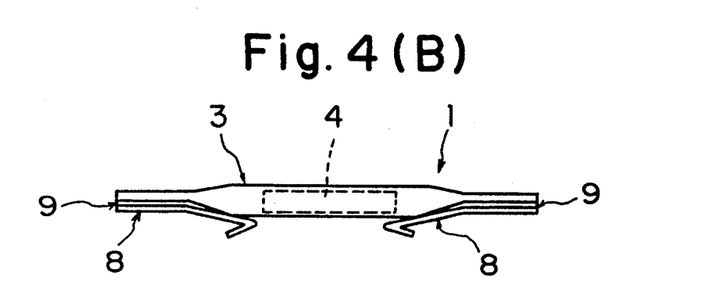

FIGS. 4(A) and 4(B) are plan and side views showing a second embodiment of the present invention.

In this embodiment, the structure of the toe-base protecting member 3 is the same as that in the first embodiment. The second embodiment is different from the first embodiment in that adhesive layers 9 are provided directly on two ends, respectively, of the protecting member 3 in place of the strips 7 of adhesive tape.

This arrangement also enables the drying member 4 to be secured in close contact with a portion between two toes by sticking the adhesive layers 8 on the top and bottom surfaces of the foot.

(Third Embodiment)

Figure 5A:
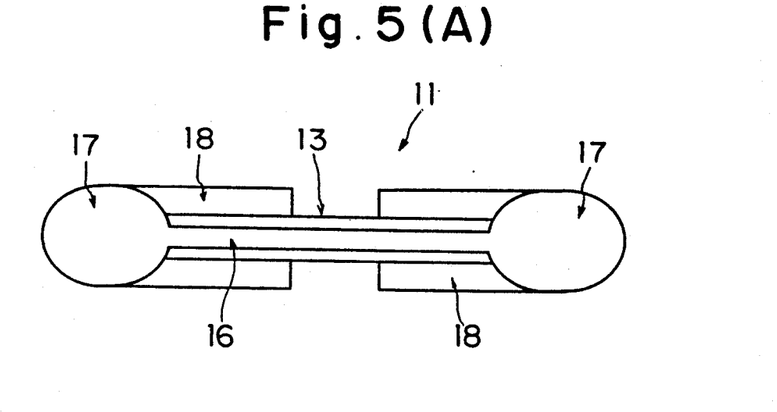
FIGS. 5(A), 5(B) and 5(C) are plan, side and rear views showing a third embodiment of the toe-base protecting device according to the present invention.
Figure 5B:
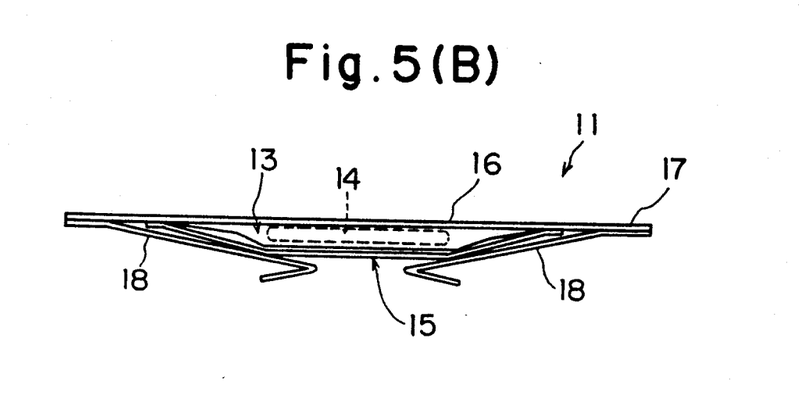
Figure 5C:
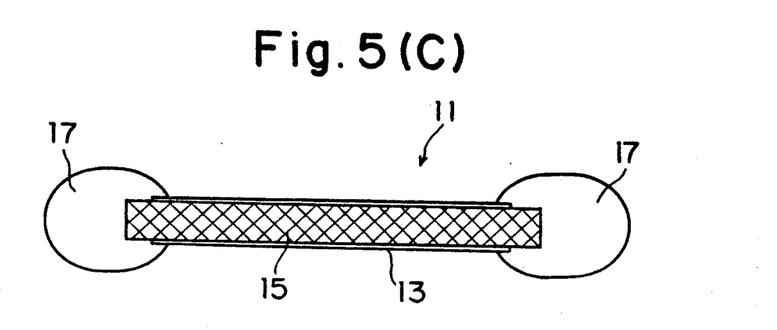

FIGS. 5(A), 5(B) and 5(C) are plan, side and rear views showing a third embodiment of the present invention (it should be noted that illustration of release paper 18 is omitted in FIG. 5(C)).

Referring to these figures, in the toe-base protecting device 11 of this embodiment, two strips 17 of adhesive tape are connected together by a connecting portion 16.

In addition, a net 15 that is formed of a synthetic resin material is bonded to the lower side of the toe-base protecting member 13. Since the net 15 is made of a synthetic resin material, it will not readily stick to the skin even if the net 15 is applied directly to it. In other words, the net 15 can be readily separated from the skin when the device 11 is removed.

Figure 6A:
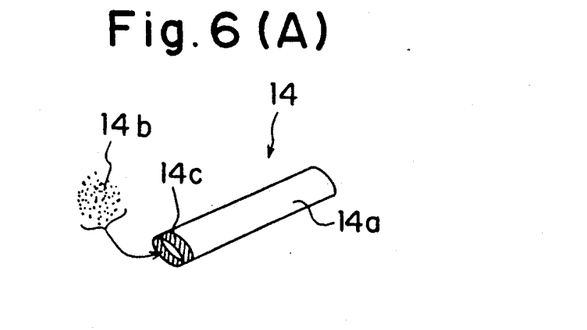
FIGS. 6(A), 6(B) and 6(C) show a method of producing the toe-base protecting device shown in FIG. 5.
Figure 6B:
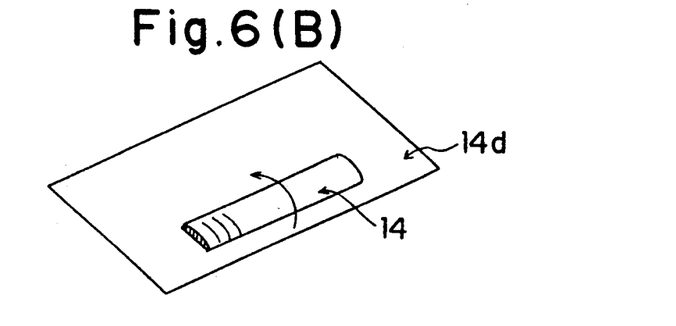
Figure 6C:
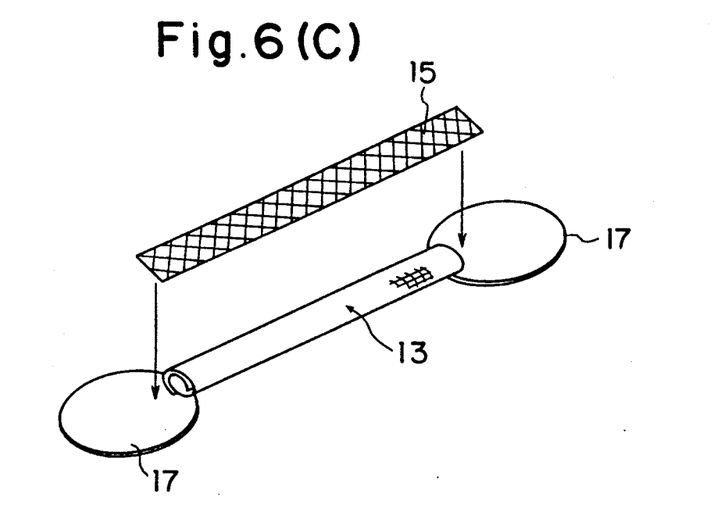

FIG. 6 shows a method of producing the toe-base protecting device 11.

First, as shown in FIG. 6(A), a cylindrical bag 14a that is formed of a hygroscopic non-woven fabric, paper or cloth is filled with activated carbon particles or powder 14b, and the mouth 14c of the bag 14a is then closed, thus completing a drying member 14.

Next, as shown in FIG. 6(B), the drying member 14 is rolled in a hygroscopic non-woven fabric (or hygroscopic paper or cloth) 14d, thereby forming a substantially rod-shaped toe-base protecting member 13.

Next, as shown in FIG. 6(C), the toe-base protecting member 13 is stuck on a connecting portion 16 (see FIG. 5(A)) that connects together two strips 17 of adhesive tape. Further, a synthetic resin net 15 is put over the protecting member 13, and two ends of the net 15 are rigidly stuck on the two strips 17 of adhesive tape.

Then, the release paper 18, shown in FIG. 5, is stuck on each strip 17 of adhesive paper, thus completing the toe-base protecting device 11 of this embodiment.

Connecting the strips 17 of adhesive tape in one unit by the connecting portion 16, as in this embodiment, facilitates the operation of bonding the toe-base protecting member 13 and the net 15 and enables mass-production to be carried out easily.

Since the net 15 is attached underneath the toe-base protecting member 13, even in a case where there is a wound in the skin of the portion between toes, there is no possibility that the toe-base protecting member 13 made of a non-woven fabric or the like will touch the wound directly. Accordingly, the toe-base protecting device 11 can be separated without the non-woven fabric sticking to the wound, thus enabling protection of the wound. It should be noted that the net 15 is not necessarily limited to the one described above and that it is possible to employ any net or sheet which is made of a synthetic resin material and provided with a large number of holes.

Although in the above-described embodiment the toe-base protecting member 13 is formed by rolling the drying member 14 in the non-woven fabric 14d, it should be noted that the protecting member 13 may comprise the drying member 14 only.

(Fourth Embodiment)

Figure 7:
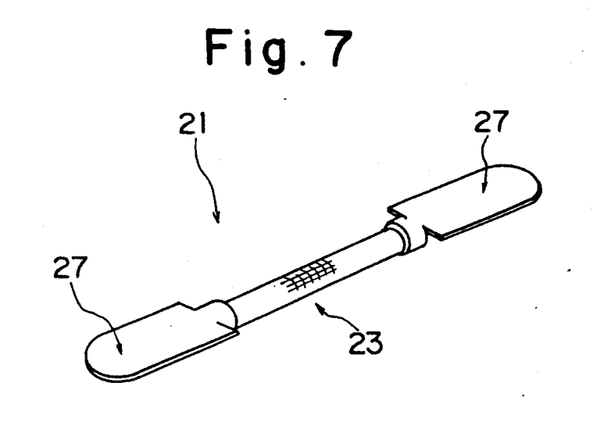
FIG. 7 is a perspective view showing a fourth embodiment of the toe-base protecting device according to the present invention.

FIG. 7 is a perspective view showing a fourth embodiment of the present invention.

As illustrated, the toe-base protecting device 21 of this embodiment is also arranged such that two strips 27 of adhesive tape are attached to two ends, respectively, of a toe-base protecting member 23 formed in a substantially rod-like shape.

Figure 8A:
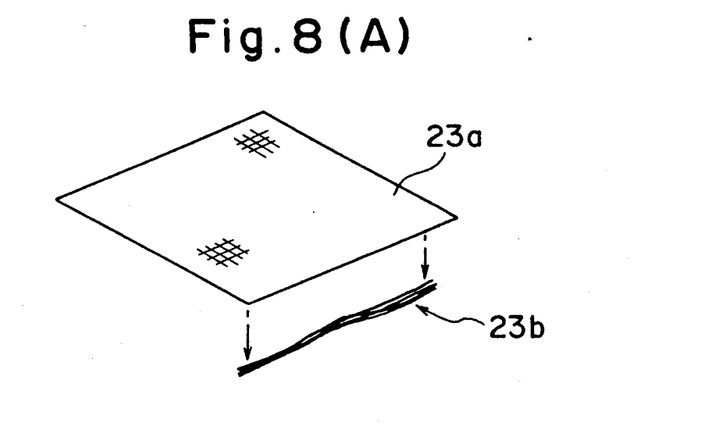
FIGS. 8(A), 8(B) and 8(C) show a method of producing the toe-base protecting device shown in FIG. 7.
Figure 8B:
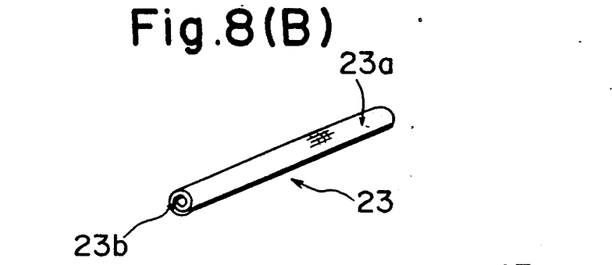
Figure 8C:
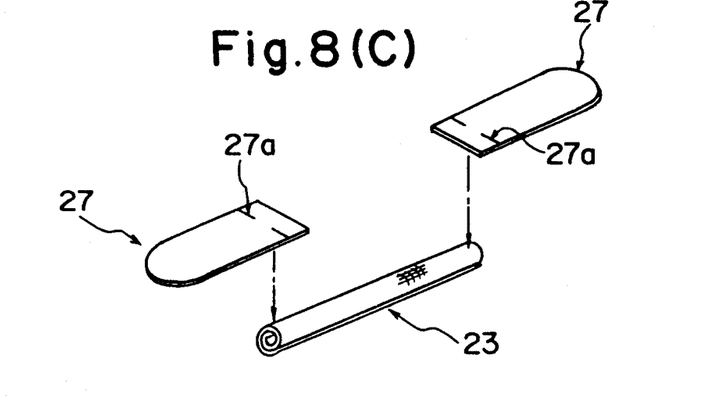

FIG. 8 shows a method of producing the toe-base protecting device 21.

First, gauze (or non-woven fabric or paper) 23a which has been sterilized at a predetermined high temperature and high pressure and sterilized cotton twisted yarn (or clean cotton or paper cotton) 23b are prepared, as shown in FIG. 8(A).

Next, as shown in FIG. 8(B), the gauze 23a is rolled up into a rod-like shape together with the twisted yarn 23b as the core, thereby forming a toe-base protecting member 23.

Next, as shown in FIG. 8(C), two strips 27 of adhesive tape are stuck on two ends, respectively, of the rod-shaped toe-base protecting member 23. In this embodiment, cuts 27a are made in each strip 27 of adhesive tape so that a portion of the strip 27 which is cut along the cuts 27a is wound around each end of the toe-base protecting member 23.

Although in this embodiment the cotton twisted yarn (or clean cotton or paper cotton) 23b is inserted in the toe-base protecting member 23, it should be noted that the twisted yarn 23b or the like is not always needed and that the protecting member 23 may comprise the gauze (or non-woven fabric or paper) 23a only.

(Fifth Embodiment)

Figure 9A:
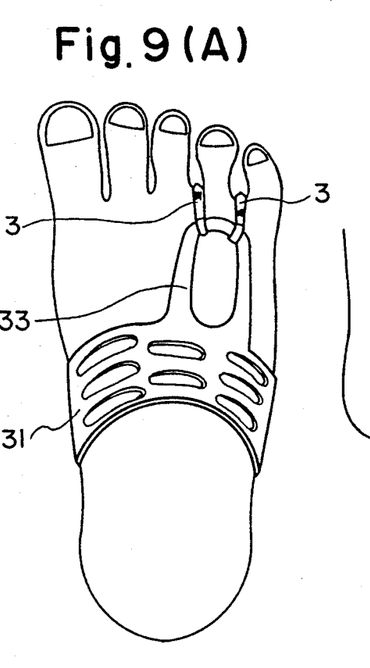
FIGS. 9(A) and 9(B) are plan and side views showing a fifth embodiment of the toe-base protecting device according to the present invention.
Figure 9B:
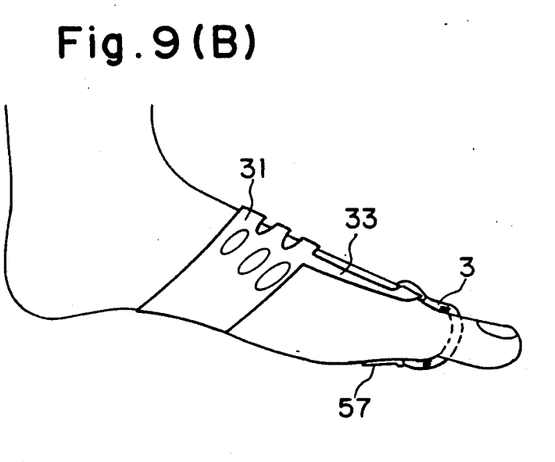

FIGS. 9(A) and 9(B) are plan and side views showing a fifth embodiment of the present invention.

In this embodiment, two toe-base protecting members 3 (13 or 23) employed in any of the foregoing embodiments are prepared, and one end of each toe-base protecting member 3 is secured to a connecting belt 33, while the other end is bonded to the bottom side of a foot by a strip 57 of adhesive tape (see FIG. 9(B)).

The connecting belt 33 is attached to a supporter 31. The supporter 31 is elastic and formed in a ring-like shape so that it is wound around the substantially central portion of a foot. The connecting belt 33 is a thin belt-like member which is made of a flexible synthetic resin material.

Employment of the supporter 31 and the connecting belt 33 makes it unnecessary to stick adhesive tape on the instep and eliminates the danger of the relatively soft skin of the instep breaking out in a rash with adhesive tape.

(Sixth Embodiment)

Figure 10:
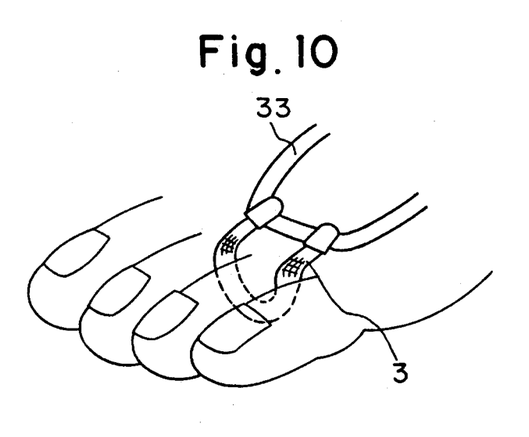
FIG. 10 is a perspective view of a sixth embodiment of the present invention.

FIG. 10 is a perspective view showing a sixth embodiment of the present invention.

In this embodiment, the supporter 31 that is shown in FIG. 9 is employed, and both ends of a single toe-base protecting member 3 (13 or 23) are attached to the connecting belt 33. In use, the looped protecting member 3 is caught on a toe so that the protecting member 3 is brought into close contact with two base portions of three adjacent toes.

This arrangement not only eliminates the need for adhesive tape but also enables a single toe-base protecting member 3 to be brought into close contact with two base portions of three adjacent toes.

The two ends of the toe-base protecting member 3 may be secured by various kinds of securing member, and various changes and modifications may be made thereto.

(Seventh Embodiment)

Figure 11:
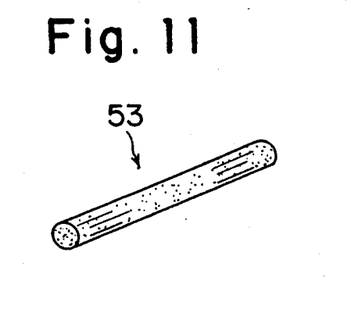
FIG. 11 is a perspective view of a toe-base protecting member that is employed in a seventh embodiment of the present invention.

A toe-base protecting member 53 such as that shown in FIG. 11 may be employed in place of the toe-base protecting member 3, 13 or 23 (or the drying member 4 or 14) employed in the foregoing embodiments.

The toe-base protecting member 53 comprises a bundle of fibers which are orientated longitudinally in a columnar shape (i.e., something like a fibrous filter that is attached directly to a cigarette) and hygroscopic particles or powder, e.g., activated carbon, which is uniformly mixed in the columnar fiber bundle.

Although the embodiments of the toe-base protecting device according to the present invention have been described in detail, it should be noted that the present invention is not necessarily limited to the described embodiments and that various changes and modifications may be imparted thereto.

For example, (1) the non-woven fabric, paper, cloth, e.g., gauze, etc. which constitutes the toe-base protecting member may be coated or impregnated with a medical substance that sterilizes the base portion between toes, or a medical substance (e.g., Amicin) that disinfects trichophyton or prevents propagation of it.

(2) In place of activated carbon that is employed in the foregoing embodiment, hygroscopic particles or powder of other materials may be employed.

Thus, it should be understood that modifications which are present within the true spirit and scope of the present invention are all included in the appended claims.

What I claim is:

1. A toe-base protecting device comprising:

a toe-base protecting member comprising a cylindrical bag that is formed of a hygroscopic and flexible material, said bag being filled with hygroscopic particles and rolled in another hygroscopic and flexible material into a substantially rod-like shape; and an adhesive tape that is provided on each end of said protecting member, said adhesive tape for sticking on a surface of a boot with said protecting member being put between toes.

2. A toe-base protecting device comprising:

a toe-base protecting member comprising a first hygroscopic and flexible material that is folded and rolled into a substantially rod-like shape with hygroscopic particles being incorporated therein to form a first plurality of circumferential layers comprising said hygroscopic particles;

said first plurality of circumferential layers being further wrapped and rolled in a second hygroscopic and flexible material to form a second plurality of circumferential layers surrounding said first plurality of circumferential layers comprising said hygroscopic particles, and thus resulting in a substantially rod-like protecting member; and an adhesive tape provided on each end of said protecting member, said adhesive tape for sticking on a surface of a foot with said protecting member being put between toes.

3. A toe-base protecting device according to claims 1 or 2, wherein said toe-base protecting member is coated or impregnated with a medicament for disinfecting and preventing propagation of trichophyton.

4. A toe-base protecting device according to claims 1 or 2, wherein the surface of at least a portion of said toe-base protecting member which touches the skin of a base portion between toes is covered with a net or sheet that is made of a synthetic resin material and is provided with a plurality of holes.

5. A toe-base protecting device according to claims 1 or 2, further comprising a connecting portion that comprises a thin belt-shaped strip of adhesive tape between said adhesive tape provided at each end of said protecting member.

6. The toe-base protecting device of claim 1, wherein said hygroscopic particles comprise activated carbon.

7. The toe-base protecting device of claim 2, wherein said hygroscopic particles comprise activated carbon.

* * * * *